US012758658B2

(12) United States Patent
Zhang et al.

(10) Patent No.: US 12,758,658 B2
(45) Date of Patent: Oct. 13, 2026

(54) DOUBLE-COMPONENT GASTRIC ULTRASOUND EXAMINATION AIDED DEVELOPER AND PREPARATION METHOD THEREFOR

(71) Applicant: Shandong Branden Medical Device Co., Ltd, Shandong (CN)

(72) Inventors: Haijun Zhang, Shandong (CN); Kunshan Yuan, Shandong (CN); Guixue Wang, Shandong (CN)

(73) Assignee: Shandong Branden Medical Device Co., Ltd., Shandong (CN)

( * ) Notice: Subject to any disclaimer, the term of this patent is extended or adjusted under 35 U.S.C. 154(b) by 488 days.

(21) Appl. No.: 18/530,233

(22) Filed: Dec. 6, 2023

(65) Prior Publication Data

US 2024/0123093 A1 Apr. 18, 2024

Related U.S. Application Data

(63) Continuation-in-part of application No. PCT/CN2023/087721, filed on Apr. 12, 2023.

(30) Foreign Application Priority Data

Oct. 13, 2022 (CN) ......................... 202211250420.6

(51) Int. Cl.
*A61K 49/22* (2006.01)

(52) U.S. Cl.
CPC .................................... *A61K 49/22* (2013.01)

(58) Field of Classification Search
CPC .............................. A61K 49/22; A61K 49/226
See application file for complete search history.

(56) References Cited

FOREIGN PATENT DOCUMENTS

| | | |
|---|---|---|
| CN | 1721000 | 1/2006 |
| CN | 102068706 | 5/2011 |
| CN | 102441180 | 1/2013 |
| CN | 104043137 | 9/2014 |
| CN | 103611173 | 5/2015 |
| CN | 105079829 | 11/2015 |
| CN | 107055553 | 8/2017 |
| CN | 107115534 | 9/2017 |
| CN | 108046276 | 5/2018 |
| CN | 109745570 | 5/2019 |
| CN | 115317629 | 11/2022 |

OTHER PUBLICATIONS

Shuai Wang, "Functionalization mesoporous silica nanomaterials, drug loading and release studies in vitro", Thesis of Master Degree, Guizhou University, Jun. 2020, pp. 1-70.

Liu, Wei-Kun et al., "Preparation of functionalized mesoporous silica nanoparticles loaded cisplatin and its killing effect on breast cancer cells", Journal of Taishan Medical College, vol. 40, No. 11, Nov. 7, 2019, pp. 801-805.

Cheng, Chun-Feng et al., "Preparation of Pickering emulsions with SiO2 nanoparticles activated with alginate derivative", China Surfactant Detergent & Cosmetics, vol. 44, No. 5, May 2014, pp. 241-246.

Shi, Shaoming, "Research on Drug Delivery System Based on Mesoporous Silica", Thesis of Master Degree, Changzhou University, Jun. 2021, pp. 1-78.

Li, Shang-Ji, "Construction of Controlled Drug Delivery Systems Based on Aminated Mesoporous Silica/Biological Macromolecules", Thesis of Master Degree, Changzhou University, May 2021, pp. 1-81.

"International Search Report (Form PCT/ISA/210) of PCT/CN2023/087721," mailed on Jun. 5, 2023, pp. 1-4.

*Primary Examiner* — James W Rogers
(74) *Attorney, Agent, or Firm* — JCIPRNET

(57) ABSTRACT

Provided are a double-component gastric ultrasound examination aided developer and a preparation method therefor, belonging to the technical field of medicine imaging diagnosis. The aided developer consists of two components, wherein component A consists of functionalized silica particles, a defoamer, sodium alginate, citric acid and water, and component B is a calcium chloride solution.

6 Claims, 1 Drawing Sheet

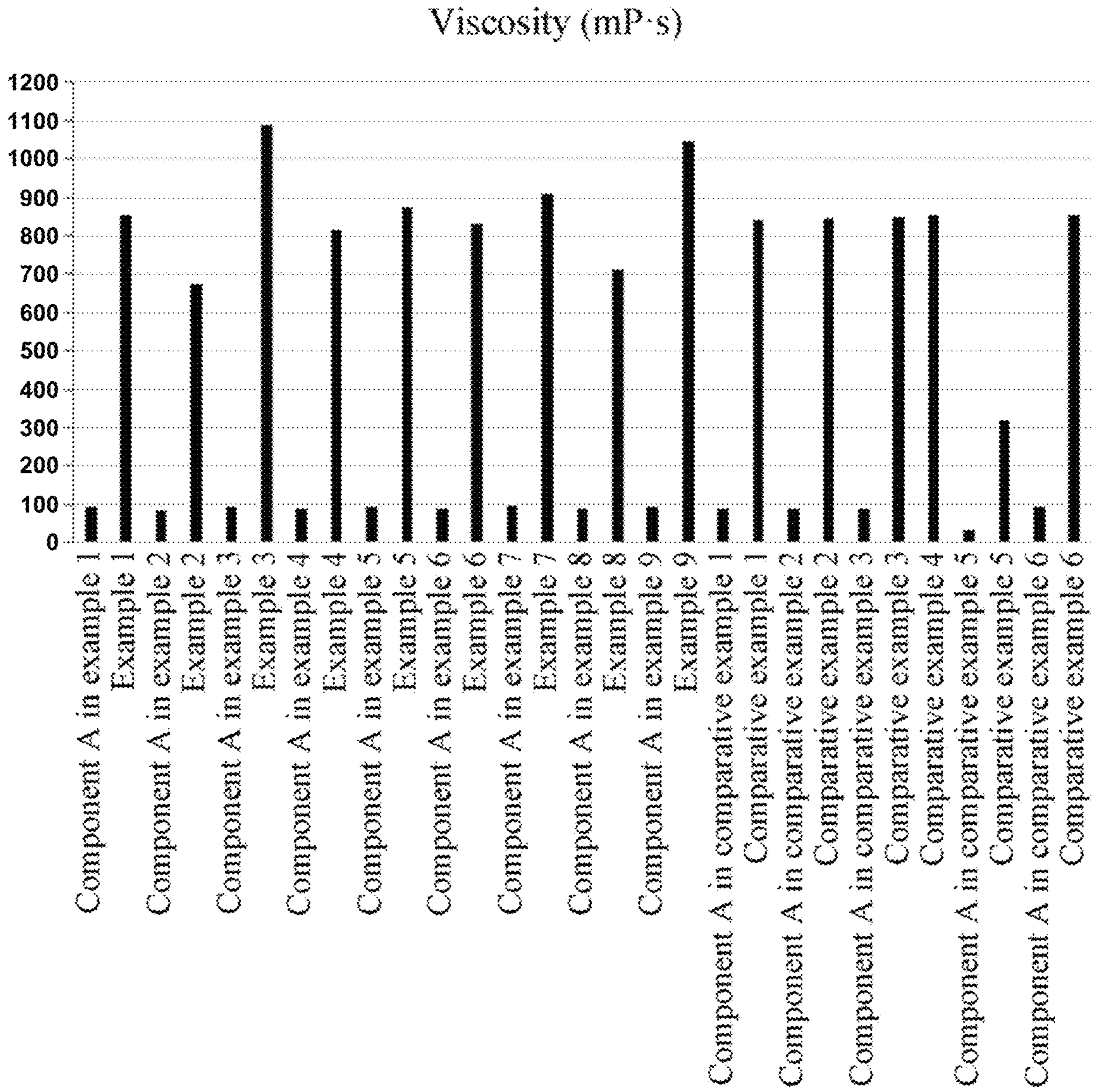
Viscosity (mP·s)
1200
1100
1000
900
800
700
600
500
400
300
200
100
0
Component A in example 1
Example 1
Component A in example 2
Example 2
Component A in example 3
Example 3
Component A in example 4
Example 4
Component A in example 5
Example 5
Component A in example 6
Example 6
Component A in example 7
Example 7
Component A in example 8
Example 8
Component A in example 9
Example 9
Component A in comparative example 1
Comparative example 1
Component A in comparative example 2
Comparative example 2
Component A in comparative example 3
Comparative example 3
Comparative example 4
Component A in comparative example 5
Comparative example 5
Component A in comparative example 6
Comparative example 6

DOUBLE-COMPONENT GASTRIC ULTRASOUND EXAMINATION AIDED DEVELOPER AND PREPARATION METHOD THEREFOR

CROSS-REFERENCE TO RELATED APPLICATION

This application is a continuation-in-part of international application of PCT application Ser. No. PCT/CN2023/087721, filed on Apr. 12, 2023, which claims the priority benefit of China application no. 202211250420.6, filed on Oct. 13, 2022. The entirety of each of the above-mentioned patent applications is hereby incorporated by reference herein and made a part of this specification.

TECHNICAL FIELD

The present disclosure relates to a double-component gastric ultrasound examination aided developer and a preparation method therefor, belonging to the technical field of medicine ultrasound examination.

DESCRIPTION OF RELATED ART

The stomach occupies ¾ of the volume of an abdominal cavity and constitutes the majority of a digestive tract, is an organ with the highest incidence rate of a digestive system, and also is one of the organs with the highest incidence rate in clinical practice. To clarify the location and nature of the lesion, different examination methods are often used to assist in diagnosis.

Methods for gastric examination include upper gastrointestinal barium meal, gastroscopy, gastric computerized tomography (CT), magnetic resonance imaging (MRI), etc. Upper gastrointestinal barium meal is convenient, less in pain and is easy to accept by patients, however, barium meal examination has radioactivity, and the examination results are affected by barium agent coating, a filling effect, and experience of an examiner Although barium sulfate is relatively safe, for a few patients, there may be adverse reactions such as allergy, barium poisoning, barium leakage, barium sulfate fecal stone incarceration, increased constipation, and complications, or even death, which limits its clinical application, especially for the elderly, constipation patients and pregnant women, as well as patients with barium allergy and acute upper gastrointestinal bleeding and other patients, X-ray barium meal examination is not used as a routine aided diagnostic method. By gastroscopy, the shape, color, lesion location, lesion size and lesion depth of gastric mucosa can be directly observed, and the lesion can be seen under direct vision, and the lesion is taken for pathological examination to determine the nature of the lesion. However, gastroscopy can only well show the structure in the cavity, and cannot observe the hierachy of the gastric wall and gastric peristalsis. Due to the fact that gastroscopy is an interventional examination, most of people experience discomfort, such as elderly patients who cannot tolerate gastroscope combined with severe heart and lung diseases, patients in the acute stage of upper gastrointestinal perforation, patients with acute severe pharyngeal disease, patients in the acute stage of corrosive esophageal injury, and patients with mental disorders who cannot cooperate, which subjectively and objectively limits the application of gastroscopy. CT/MRI examination has high spatial resolution and clear anatomical structure display, and is a commonly used imaging detection method for gastric cancer staging. However, CT/MRI examination difficultly detects small lesions in the gastric cavity and has little diagnostic value for other gastric diseases, and therefore it is not used as a routine examination method.

Since the discovery of piezoelectricity and anti-piezoelectricity in physics at the beginning of the 20th century, the history of ultrasonic technology has been quickly opened. Because of no invasion, no pain, low price, good tolerance and no radioactivity, it has become a common and important inspection method in the substantive organs of the digestive system.

At present, the gastric ultrasound examination in clinical application mainly includes three methods: transabdominal gastric ultrasound examination, gastric filling ultrasound examination, and endoscopic ultrasound examination. Abdominal wall gastric ultrasound examination is only for preliminary screening; endoscopic ultrasound examination combines the advantages of endoscopy and ultrasound, making up for their respective shortcomings and further improving the diagnostic level of endoscopy and ultrasound. However, due to its expensive price, complex operation, and certain trauma, it is only limited to some large hospitals and far from being popularized; gastric filling ultrasound examination is a method to fill the stomach cavity with a contrast agent (also known as an aided developer), eliminate the interference of gases and contents in the stomach cavity to ultrasound, improve the internal environment of gastric ultrasound imaging, so as to achieve a clearer display of gastric wall structure and its lesions. This technology is in a development trend for ultrasonic examination of gastric diseases, and can be popularized. The contrast agents mainly include an echo-free water dosage form and an echo powder dosage form. In current, the echo powder dosage form is mainly applied.

At present, contrast agents in the Chinese market are mainly prepared by grinding, mixing and blending the existing local traditional Chinese medicine or ingredients, such as Chinese herbal formulas described in CN102441180B and CN103611173B, which have certain health and therapeutic effects. The aided developer described in CN1721000A is made by grinding, mixing and blending food ingredients, and has good ultrasound image display effect, but it needs to be brewed with 90-100° C. boiling water before use and is quickly stirred to form a uniform paste solution, and then after cooling to a suitable temperature (usually controlled at 30-50° C.), the patient is advised to drink or take the ultrasound examination while taking the aided developer.

In addition to the traditional Chinese medicine or food aided developers, aided developers that are more convenient to use and better in effect are developed. For example, the aided developer in patent CN107115534A uses the combination of an osmotic pressure contrast agent, a swelling substance, a stabilizer and a defoamer to obtain an aided developer with a good compatibility and a filling effect. In patent CN109745570A, besides use of an osmotic pressure contrast agent, a solid contrast material is added to increase the development effect, and bioactive substances such as bioactive glass, fructooligosaccharide and hyaluronic acid are introduced to play a certain role in health care.

However, there are certain limitations for various types of aided developers, for example the traditional Chinese medicine aided developer has a good health effect, but its display interface under the ultrasound is a low-echo interface with limited aided developing effect; aided developers for food are complicated to operate and long in waiting time; aided developers where solid contrast agents are added firstly need to have an appropriate solid contrast particle size, the developing effect is not good if the solid contrast particles are too small or too large, that is to say, the brightness of the developing interface is too low if the solid contrast particles are too small, and the particle feeling of the developing interface is too strong if the solid contrast particles are too large; in addition, the density of the solid contrast material should be matched with an aided developer liquid system, mismatched density can affect the uniformity of the product, i.e., the solid contrast material in the liquid aided developer is prone to sinking if the density is too high, while the solid contrast material in the liquid aided developer is prone to floating if the density is too low; finally, the aided developer needs to add swelling substances to increase the window period, however, when the viscosity of the aided developer system remains high, the gas in the stomach is difficult to expel, which easily causes artifacts so as to affect the developing effect, moreover when the solid contrast material sinks or floats due to high or low density, it is difficult to shake well. When the viscosity of the aided developer system remains low, it easily leads to a too short window period, and the stomach quickly empties the aided developer, thereby causing difficulties brought by gastric ultrasound diagnosis from clinical doctors.

SUMMARY

For the shortcomings of the existing technology mentioned above, the objective of the present disclosure is to provide a double-component gastric ultrasound examination aided developer which has a stronger gastric wall aided developing effect, is a stable and uniform product, is easy to expel excessive gas in the stomach during the use, and can increase the window period.

In order to achieve the above objective, the present disclosure adopts the following technical solution:

Provided is a double-component gastric ultrasound examination aided developer, the aided developer consists of two components: component A and component B, wherein the component A consists of functionalized silica particles, a defoamer, a preservative, sodium alginate, citric acid and water; and the component B is a calcium chloride solution. The density of the functionalized silica particles is the same as that of the component A liquid of the aided developer.

By utilizing characteristics that the component A has low viscosity and comprises a defoamer, the aided developer of the present disclosure may expel a gas quickly while filling the stomach in order to reduce the interference of a gas artifact; at the same time accompanied by gastric peristalsis, the functionalized silica particles may be quickly dispersed to the stomach wall to be adhered to the lipoprotein layer of the stomach wall under the actions of an aldehyde group or a mercapto group and prolamin, so as to form a uniform and high-echo interface on the stomach wall, thereby improving the disease diagnosis rate. After the component B is used, the viscosity of the aided developer increases, the window period is prolonged, and the sufficiency of the examination time is ensured.

Further, the functionalized silica particles are biocompatible polymer modified silica particles, and the functionalized silica particles are 0.5-1.5% by mass of the component A.

Further, in the biocompatible polymer modified silica particles, the diameter size of silica is 70-90 meshes.

Further, the defoamer is at least one of an organosilicon defoamer and a polyether defoamer, the organosilicon defoamer may be dimethylsiloxane, etc., and the polyether defoamer may be polyoxypropylene oxyethylene glycol ether, etc. The defoamer is 0.02-0.04% by mass of the component A.

Further, the viscosity of 1% sodium alginate aqueous solution is 100-200 mPa·s, and the sodium alginate is 0.5-1% by mass of the component A.

Further, the citric acid is 4.2-6% by mass of the component A.

Further, the concentration of the calcium chloride solution is 12.5-18% by mass of the component B.

Further, a volume ratio of the component A to the component B in the aided developer is 9:1, and the component A and the component B are separately packaged.

Further, a mass ratio of citric acid to calcium chloride in the aided developer is 3:1.

Further, the preservative is deoxidized sodium acetate which is 0.03-0.05% by mass of the component A.

Further, the biocompatible polymer is one or more of polyethylene glycol, branched polyethylene glycol, chitosan and hyaluronic acid.

Further, the biocompatible polymer is modified by grafting of an aldehyde group and prolamin, or grafting of a sulfydryl group and prolamin. The grafting rate of the aldehyde group or the sulfydryl group occupies 10-20% of the active group of the biocompatible polymer, and the grafting rate of the prolamin occupies 5-10% of the active group of the biocompatible polymer.

Further, the active groups of polyethylene glycol and branched polyethylene glycol are hydroxyl groups, the active group of the chitosan is an amino group, and the active group of the hyaluronic acid is a carboxyl group.

Further, before the component A is mixed with the component B, the viscosity of the component A is less than or equal to 100 mPa·s, and after the component A is sufficiently mixed with the component B, the viscosity of the aided developer is more than or equal to 500 mPa·s.

Further, a preparation method for the double-component gastric ultrasound examination aided developer, comprising the following steps of:

(1) taking pure water, adding citric acid at 50-100 rpm, adjusting a rotation speed to 800-1200 rpm after citric acid is dissolved, adding sodium alginate many times in a small amount, then adjusting the rotation speed to 30-60 rpm, heating the solution to 90° C. under the continuous stirring, adjusting the rotation speed to 50-100 rpm after sodium alginate is completely dissolved, then adding functionalized silica particles, a defoamer and a preservative to be sufficiently mixed with the solution to obtain component A;

(2) dissolving calcium chloride into pure water at 50-100 rpm to obtain unsterilized component B; and (3) respectively charging the component A and the unsterilized component B into a polyester bottle; and sterilizing the unsterilized component B under the electronic irradiation of 15-25K to obtain component B.

When in examination, the component A is first used, the viscosity of the component A is relatively low, so it may expel a gas quickly while filling the stomach in order to reduce the interference of a gas artifact; at the same time accompanied by gastric peristalsis, the functionalized silica particles may be quickly dispersed to the stomach wall to be adhered to the lipoprotein layer of the stomach wall under the actions of an aldehyde group or a mercapto group and prolamin, so as to form a uniform and high-echo interface on the stomach wall, thereby improving the disease diagnosis rate. The component B is used after the component A is used for 3 minutes, the viscosity of the aided developer increases in 1-3 minutes, a window period is prolonged, and the sufficiency of examination time is ensured.

The present disclosure has the beneficial effects:

1. The aided developer of the present disclosure has a good aided developing effect on the gastric wall. Through document retrieval, in vitro and in vivo experience, silica particles with specific particle size are selected and modified with biocompatible polymers grafted with specific functional groups, so that the surface area of the silica particle is increased by using biocompatible polymers, and the adhesion between silica particles and the lipoprotein layer of the gastric wall is increased by using the aldehyde group or the mercapto group and prolamin, accompanied by gastric peristalsis, the functionalized silica particles can be quickly dispersed and adhere to the gastric wall to form the uniform and high-echo interface, thereby improving the diagnosis rate of diseases.
2. The aided developer of the present disclosure does not cause the rising or falling of solid contrasts, thereby ensuring the uniformity and stability of the product. The use of biocompatible polymers are used to modify silica particles ensures that the density of the silica particles is the same as that of component A liquid, without settling or floating during the storage, thereby ensuring the stability of the product.
3. The aided developer described in the present disclosure can expel excessive gas from the stomach while ensuring a sufficient window period, reducing the impact of the gas artifact on the aided developing effect of gastric ultrasound diagnosis. The component A has an initial viscosity of less than or equal to 100 mPa·s and comprises the defoamer. After entering the stomach, the component A can rapidly expel the gas while filling the stomach, so as to reduce the interference of the gas artifact. After use of the component B, under the actions of citric acid and calcium ions, the cross-linking degree of sodium alginate is increased, the viscosity of the aided developer is increased, and the window period is prolonged, thereby ensuring the sufficiency of the examination time.

BRIEF DESCRIPTION OF THE DRAWINGS

The FIGURE is a viscosity diagram of a double-component gastric ultrasound examination aided developer and its component A at 37±0.2° C.

DESCRIPTION OF THE EMBODIMENTS

Next, the present disclosure will be further illustrated in combination with embodiments, and it should be noted that the following description is only for explaining the present disclosure but not limiting the contents of the present disclosure.

Unless otherwise specified, in the biocompatible polymer modified silica particles used in examples and comparative examples, the particle size of silica is 70-90 meshes; a volume ratio of component A to component B in the aided developer is 9:1; a mass ratio of citric acid to calcium chloride in the aided developer is 3:1.

EXAMPLE 1

A certain amount of pure water was taken, citric acid (the mass fraction of citric acid in component A was 5%) was added in 50-100 rpm, a rotation speed was adjusted to 800-1200 rpm after citric acid was dissolved, sodium alginate with a viscosity of 1% aqueous solution being 150 mP·s (the mass fraction of sodium alginate in component A was 0.7%) was added for many times in a small amount, then the rotation speed was adjusted to 30-60 rpm, the solution was heated to 90° C. under the continuous stirring, the rotation speed was adjusted to 50-100 rpm after sodium alginate was completely dissolved, then polyethylene glycol functionalized silica particles (the mass fraction of functionalized silica particles in component A was 1%) with a sulfhydryl group grafting rate of 15% and a prolamin grafting rate of 7.5%, dimethylsiloxane (the mass fraction of dimethylsiloxane in component A was 0.03%) and deoxidized sodium acetate (the mass fraction of deoxidized sodium acetate in component A was 0.04%) were added so that the functionalized silica particles, dimethylsiloxane and deoxidized sodium acetate were sufficiently mixed to obtain component A, wherein the density of the functionalized silica particles was the same as that of the component A liquid; calcium chloride (the mass fraction of calcium chloride in component B was 15%) was dissolved into purified water at 50-100 rpm to obtain unsterilized component B; the component A and the unsterilized component B were respectively charged into a polyester bottle respectively; and the unsterilized component B was irradiated under the electron beam to be sterilized at 20K to obtain the component B.

EXAMPLE 2

A certain amount of pure water was taken, citric acid (the mass fraction of citric acid in component A was 4.2%) was added in 50-100 rpm, a rotation speed was adjusted to 800-1200 rpm after citric acid was dissolved, sodium alginate with a viscosity of 1% aqueous solution being 200 mP·s (the mass fraction of sodium alginate in component A was 0.5%) was added for many times in a small amount, then the rotation speed was adjusted to 30-60 rpm, the solution was heated to 90° C. under the continuous stirring, the rotation speed was adjusted to 50-100 rpm after sodium alginate was completely dissolved, then chitosan functionalized silica particles (the mass fraction of functionalized silica particles in component A was 0.5%) with an aldehyde group grafting rate of 20% and a prolamin grafting rate of 5%, polyoxypropylene oxyethylene glycol ether (the mass fraction of polyoxypropylene oxyethylene glycol ether in component A was 0.02%) and deoxidized sodium acetate (the mass fraction of deoxidized sodium acetate in component A was 0.05%) were added so that the functionalized silica particles, polyoxypropylene oxyethylene glycol ether and deoxidized sodium acetate were sufficiently mixed to obtain component A, wherein the density of the functionalized silica particles was the same as that of the component A liquid; calcium chloride (the mass fraction of calcium chloride in component B was 12.5%) was dissolved into purified water at 50-100 rpm to obtain unsterilized component B; the component A and the unsterilized component B were respectively charged into a polyester bottle respectively; and the unsterilized component B was irradiated under the electron beam to be sterilized at 25K to obtain the component B.

EXAMPLE 3

A certain amount of pure water was taken, citric acid (the mass fraction of citric acid in component A was 6%) was added in 50-100 rpm, a rotation speed was adjusted to 800-1200 rpm after citric acid was dissolved, sodium alginate with a viscosity of 1% aqueous solution being 100 mP·s (the mass fraction of sodium alginate in component A was 1%) was added for many times in a small amount, then the rotation speed was adjusted to 30-60 rpm, the solution was heated to 90° C. under the continuous stirring, the rotation speed was adjusted to 50-100 rpm after sodium alginate was completely dissolved, then hyaluronic acid functionalized silica particles (the mass fraction of functionalized silica particles in component A was 1.5%) with a sulfhydryl group grafting rate of 10% and a prolamin grafting rate of 10%, dimethylsiloxane (the mass fraction of dimethylsiloxane in component A was 0.04%) and deoxidized sodium acetate (the mass fraction of deoxidized sodium acetate in component A was 0.03%) were added so that the functionalized silica particles, dimethylsiloxane and deoxidized sodium acetate were sufficiently mixed to obtain component A, wherein the density of the functionalized silica particles was the same as that of component A liquid; calcium chloride (the mass fraction of calcium chloride in component B was 18%) was dissolved into purified water at 50-100 rpm to obtain unsterilized component B; the component A and the unsterilized component B were respectively charged into a polyester bottle respectively; and the unsterilized component B was irradiated under the electron beam to be sterilized at 15K to obtain the component B.

EXAMPLE 4

Others were all the same as those in example 1 except that the functionalized silica particles were polyethylene glycol functionalized silica particles with a sulfhydryl group grafting rate of 10% and a prolamin grafting rate of 5%, and the mass fraction of the functionalized silica particles in component A was 0.5%, wherein the density of the functionalized silica particles was the same as that of component A liquid.

EXAMPLE 5

Others were all the same as those in example 1 except that the functionalized silica particles were polyethylene glycol functionalized silica particles with a sulfhydryl group grafting rate of 20% and a prolamin grafting rate of 10%, and the mass fraction of the functionalized silica particles in component A was 1.5%, wherein the density of the functionalized silica particles was the same as that of component A liquid.

EXAMPLE 6

Others were all the same as those in example 1 except that the mass fraction of sodium alginate in component A was 0.5%, and the viscosity of 1% sodium alginate aqueous solution was 200 mP·s.

EXAMPLE 7

Others were all the same as those in example 1 except that the mass fraction of sodium alginate in component A was 1%, and the viscosity of 1% sodium alginate aqueous solution was 100 mP·s.

EXAMPLE 8

Others were all the same as those in example 1 except that the mass fraction of sodium citrate in component A was 4.2%, and the mass fraction of calcium chloride in component B was 12.5%.

EXAMPLE 9

Others were all the same as those in example 1 except that the mass fraction of sodium citrate in component A was 6%, and the mass fraction of calcium chloride in component B was 18%.

COMPARATIVE EXAMPLE 1

Others were all the same as those in example 1 except that silica particles were not functionalized.

COMPARATIVE EXAMPLE 2

Others were all the same as those in example 1 except that silica particles were modified by using polyethylene glycol, without grafting of a sulfhydryl group and prolamin.

COMPARATIVE EXAMPLE 3

Others were all the same as those in example 1 except that silica particles were modified by using polyethylene glycol, the sulfhydryl group grafting rate of polyethylene glycol was 5% and the prolamin grafting rate of polyethylene glycol was 2.5%.

COMPARATIVE EXAMPLE 4

Others were all the same as those in example 1 except that the component A and the component B were provided in a mixing state.

COMPARATIVE EXAMPLE 5

Others were all the same as those in example 1 except that the mass fraction of sodium alginate in component A was 0.2%.

COMPARATIVE EXAMPLE 6

Others were all the same as those in example 1 except that no defoamer was added.

The biocompatible polymer modified silica particles can be prepared by referring to the methods described in "RESEARCH ON FUNCTIONALIZATION OF MESOPOROUS SILICA NANO MATERIALS AND DRUG CARRYING AND IN VITRO RELEASE" (Wang Shuai. Research on Functionalization of Mesoporous Silica Nano materials and Drug Carrying and in vitro Release [D]. Guizhou University, 2020), "THIOL CARBOXYL DOUBLE MODIFIED MESOPOROUS SILICA NANOPARTICLES AND ITS PREPARATION METHOD" (CN107055553A), "PREPARATION OF CARBOXYL TERMINATED POLYETHYLENE GLYCOL MODIFIED MESOPOROUS SILICA NANOPARTICLE AND USE THEREOF" (CN108046276A), "RESEARCH ON MESOPOROUS SILICA-BASED DRUG LOADING SYSTEM" (Shi Shaoming. Research on Mesoporous Silica-based Drug Loading System [D]. Changzhou University, 2021), "CONSTRUCTION OF AMINATED MESOPOROUS SILICA/BIOMACROMOLECULAR BASED DRUG-CONTROLLED RELEASE SYSTEM" (Li Shangji. Construction Of Aminoated Mesoporous Silica/Biomacromolecular Based Drug Controlled Release System [D]. Changzhou University, 2021), "PREPARATION OF PICKERING LOTION FROM ALGINIC ACID DERIVATIVES ACTIVATING SILICA NANOPARTICLES (Cheng Chun-feng, Li Ka-shing, Yan Huigiong, Liu Ruolin, Wang Chunxiu, Lin Qiang. Preparation of Pickering lotion from Alginic acid Derivatives Activating Silica Nanoparticles [J]. Daily Chemical Industry, 2014, 44 (05): 241-246.).

According to the "YY/T 0681.1-2018 Test Methods for Sterile Medical Device Packaging-Part 1: Guidelines for Accelerated Aging Testing", with a 2-year validity period as the goal, the gastric ultrasound examination aided developers prepared in examples 1-9 and comparative examples 1-6 were subjected to accelerated aging at 60° C. for 65 days, and the uniformity of the samples after aging was recorded. The results are as shown in Table 1

TABLE 1

Uniformity of samples after accelerated aging

| Group | After accelerated aging Uniformity of samples | Note |
|---|---|---|
| Example 1 | Uniform | / |
| Example 2 | Uniform | / |
| Example 3 | Uniform | / |
| Example 4 | Uniform | / |
| Example 5 | Uniform | / |
| Example 6 | Uniform | / |
| Example 7 | Uniform | / |
| Example 8 | Uniform | / |
| Example 9 | Uniform | / |
| Comparative example 1 | Non-uniform | Sinking of solid particles |
| Comparative example 2 | Uniform | / |
| Comparative example 3 | Uniform | / |
| Comparative example 4 | Non-uniform | Floating of solid particles |
| Comparative example 5 | Uniform | / |
| Comparative example 6 | Uniform | / |

It can be seen from Table 1 that in examples 1-9 and comparative example 2, comparative example 3, comparative example 5 and comparative example 6, samples after accelerated aging were uniform, without floating or sinking of solid particles. In comparative example 1, the silica particles had no functional modification and their density was higher than that of component A liquid, thereby resulting in sinking of solid particles. In comparative example 4, the component A and the component B were stored in a mixed state. The sample maintained a relatively persistent uniformity for a long period of time due to the overall high viscosity in the beginning, but after complete aging, the functionalized silica particles ultimately showed floating of solid particles due to their lower density compared to the mixed solution.

At 37±0.2° C., the viscosity of the gastric ultrasound examination aided developer was measured after the component A and the component B in examples 1-9 and comparative examples 1-6 were mixed, as shown in the FIGURE.

It can be seen from the FIGURE in that at 37±0.2° C., the viscosity of the component A in examples 1-9, comparative examples 1-3 and comparative examples 5-6 was less than 100 mPa·s, the viscosity after two components in examples 1-9, comparative examples 1-4 and comparative example 6 were mixed was more than 500 mPa·s, comparative example 4 itself was a sample after two components were mixed which had no related viscosity data of the component A, the concentration of sodium alginate in comparative example 5 was too low, and the requirement that the viscosity was larger than or equal to 500 mPa·s could not be met after the two components were mixed.

The developing effect of the gastric ultrasound examination aided developer prepared in examples 1-3 and comparative examples 1-6 were detected, and the specific method was as follows:

Except for the sample described in comparative example 4, 4 bottles of 450 ml component A sample and 50 ml component B sample were prepared for each group; 4 bottles of double-component mixed samples were prepared in comparative example 4. An animal experiment adopted 4 beagle dogs, ♀22/♂2 month old, about 10 kg in weight. Except for the sample group described in comparative example 4, 450 ml of component A sample was administered by gavage 15 minutes before imaging examination, 50 ml of component B sample was administered after 3 min, and ultrasound examination was performed after component B was administered 3 min to observe the filling situation of the stomach. The sample group described in comparative example 4 was directly administered with 500 ml of drug, and after 6 min of administration, the filling situation of the stomach was observed.

The scoring criteria for gastric wall hierarchy and structure, gastric morphology, peristalsis and emptying function display, window time satisfaction, and gas artifact elimination effect are shown in Table 2. The higher the score, the better the ability.

TABLE 2 standard for effect scoring

| Item | Score | Judgment criteria |
|---|---|---|
| Hierarchy and structure | 0 score | The hierarchy and structure of the stomach wall cannot completely be observed |
| | 2 scores | The hierarchy and structure of the stomach wall can be observed, but is difficultly distinguished |
| | 4 scores | The hierarchy and structure of the stomach wall is difficultly distinguished to a certain degree |
| | 6 scores | The hierarchy and structure of the stomach wall is distinguished to a certain degree |
| | 8 scores | The hierarchy and structure of the stomach wall is relatively clearly distinguished |
| | 10 scores | The hierarchy and structure of the stomach wall is completely clearly distinguished |
| Morphology | 0 score | The morphology of stomach cannot be completely observed |
| | 1 score | The morphology of stomach cannot be observed, but is difficultly distinguished |
| | 2 scores | The morphology of stomach is difficultly distinguished to a certain degree |

TABLE 2-continued

| standard for effect scoring | | |
|---|---|---|
| Item | Score | Judgment criteria |
| | 3 scores | The morphology of stomach is distinguished to a certain degree |
| | 4 scores | The morphology of stomach is relatively clearly distinguished to a certain degree |
| | 5 scores | The morphology of stomach is completely clearly distinguished to a certain degree |
| Peristaltic and evacuation function display | 0 score | Peristaltic and evacuation function of stomach cannot be completely observed |
| | 1 score | Peristaltic and evacuation function of stomach can be observed, but is difficultly judged. |
| | 2 scores | Peristaltic and evacuation function of stomach is difficultly judged to a certain degree |
| | 3 scores | Peristaltic and evacuation function of stomach is distinguished to a certain degree |
| | 4 scores | Peristaltic and evacuation function of stomach is relatively clearly distinguished to a certain degree |
| | 5 scores | Peristaltic and evacuation function of stomach is completely clearly distinguished to a certain degree |
| Satisfaction degree of effective inspection window time | 0 score | Stomach window time cannot completely meet observation requirement |
| | 1 score | Stomach window time still has great shortage relative to observation requirement |
| | 2 scores | Stomach window time can meet observation requirement as soon as possible |
| | 3 scores | Stomach window time just meets observation requirement at normal speed |
| | 4 scores | Relatively sufficient stomach window time just can meet observation requirement at normal speed |
| | 5 scores | Stomach window time can meet observation requirement at normal speed |
| Elimination of the gas artifact | 0 score | The gas artifact cannot be completely eliminated |
| | 1 score | The gas artifact is slightly eliminated, but the gas artifact still affects ultrasound observation of the gastrointestinal tract |
| | 2 scores | The gas artifact is moderately eliminated, but the observation effect of the gas artifact on the gastrointestinal tract is limited |
| | 3 scores | The gas artifact is moderately eliminated, but there is no observation effect of the gas artifact on the gastrointestinal tract. |
| | 4 scores | The gas artifact can be eliminated |
| | 5 scores | The gas artifact can be completely eliminated |

Developing effects of examples 1-3 and comparative examples 1-6 are seen in Table 3 below.

TABLE 3

| Developing effect | | | | | | |
|---|---|---|---|---|---|---|
| Group | Hierarchy and structure | Morphology | Peristaltic and evacuation function display | Satisfaction degree of effective inspection window time | Elimination of gas artifact | Average score |
| Example 1 | 10 | 5 | 5 | 5 | 5 | 6 |
| Example 2 | 10 | 5 | 5 | 4.75 | 5 | 5.95 |
| Example 3 | 10 | 5 | 5 | 5 | 4.75 | 5.95 |
| Comparative example 1 | 4 | 2 | 3.25 | 1 | 5 | 3.05 |
| Comparative example 2 | 5.5 | 4 | 3.5 | 3.75 | 5 | 4.35 |
| Comparative example 3 | 6 | 4.25 | 3.75 | 4 | 5 | 4.6 |
| Comparative example 4 | 6 | 5 | 5 | 4 | 0 | 4 |
| Comparative example 5 | 10 | 5 | 5 | 1 | 5 | 5.2 |
| Comparative example 6 | 10 | 5 | 5 | 4.25 | 1 | 5.05 |

It can be seen from Table 3 that the average score of examples 1-3 exceeds 5.5 scores. From various scores, it can be seen that the imaging effect of the sample described in examples 1-3 is as follows: it can completely and clearly distinguish the level and structure of the gastrointestinal wall, the morphology of various parts of the gastrointestinal tract, gastrointestinal peristalsis, and emptying function; almost completely eliminate the gas artifact; and has sufficient gastric window time to meet the needs of normal speed observation. The average scores of comparative examples 1-6 are 3.05, 4.35, 4.6, 4, 5.2, and 5.05, respectively, which are much lower than the scores of examples 1-3. From various scores, it can be seen that the silica particles in comparative example 1 are not functionalized. After the component A enters the stomach, it cannot form specific adhesion with the gastric wall. Therefore, after the component B is added, it can only be suspended in the gastric cavity. Due to the low content of silica particles themselves, their scores, except for the good effect of eliminating the gas artifact, have significantly decreased compared to examples 1-3; compared to comparative example 1, although silica particles in comparative example 2 have no specific functional group modification, they have biocompatible polymer modification, and their density is relatively close to the sample liquid. In addition to the gas artifact elimination effect score, other scores have been improved; compared to comparative example 2, the silica particles in comparative example 3 have a certain degree of specific functional group modification, but the functional group content is lower compared to examples 1-3, so its score is between comparative example 2 and examples 1-3; comparative example 4 is a two component premixed sample with a high initial viscosity when entering the stomach, making it unable to expel gas. Meanwhile, the proportion of the functionalized silica particles adhering to the gastric wall is also low, so the hierarchical structure of its gastric wall, effective examination window time satisfaction and gas artifact elimination effect are lower than those of examples 1-3; the content of sodium alginate in comparative example 5 is relatively low. Although it can better expel the gas from the stomach, and the functionalized silica particles can well adhere to the stomach wall, its final viscosity is low, which cannot meet the effective examination window time; there is no defoamer in comparative example 6, so its effectiveness for eliminating the gas artifact is poor.

The above-mentioned examples are some examples of the present disclosure, but not all. The detailed description of the examples of the present disclosure is not intended to limit the scope of protection of the present disclosure, but only for indicating the selected examples of the present disclosure. Based on examples in the present disclosure, all other examples obtained by persons of ordinary skill in the art are included within the scope of protection of the present application without creative efforts.

What is claimed is:

1. A double-component gastric ultrasound examination aided developer, consisting of two components,

- a component A consists of functionalized silica particles, a defoamer, a preservative, sodium alginate, citric acid and water; and
- a component B is a calcium chloride solution,
- wherein a density of the functionalized silica particles is the same as a liquid density of the component A;
- the functionalized silica particles are biocompatible polymer modified silica particles, which are 0.5-1.5% by mass of the component A;
- in the biocompatible polymer modified silica particles, a diameter size of silica is 70-90 meshes,
- the biocompatible polymer is one or more of polyethylene glycol, branched polyethylene glycol, chitosan and hyaluronic acid; the biocompatible polymer is modified by grafting of an aldehyde group and prolamin, or grafting of a sulfydryl group and prolamin, a grafting rate of the aldehyde group or the sulfydryl group occupies 10-20% of an active group of the biocompatible polymer, and a grafting rate of the prolamin occupies 5-10% of the active group of the biocompatible polymer;
- active groups of polyethylene glycol and branched polyethylene glycol are hydroxyl groups, the active group of the chitosan is an amino group, and the active group of the hyaluronic acid is a carboxyl group;
- sodium alginate is 0.5-1% by mass of the component A, and a viscosity of an 1% sodium alginate aqueous solution is 100-200 mPa·s;
- citric acid is 4.2-6% by mass of the component A;
- a concentration of the calcium chloride solution in the component B is 12.5-18% by mass;
- a volume ratio of the component A to the component B in the double-component gastric ultrasound examination aided developer is 9:1; and
- a mass ratio of citric acid to calcium chloride in the double-component gastric ultrasound examination aided developer is 3:1.

2. The double-component gastric ultrasound examination aided developer according to claim 1, wherein the defoamer is at least one of an organosilicon defoamer and a polyether defoamer; and the defoamer is 0.02-0.04% by mass of the component A.

3. The double-component gastric ultrasound examination aided developer according to claim 2, wherein the organosilicon defoamer is dimethylsiloxane, and the polyether defoamer is polyoxypropylene oxyethylene glycol ether.

4. The double-component gastric ultrasound examination aided developer according to claim 1, wherein the preservative is deoxidized sodium acetate which is 0.03-0.05% by mass of the component A.

5. The double-component gastric ultrasound examination aided developer according to claim 1, wherein before the component A is mixed with the component B in the double-component gastric ultrasound examination aided developer, a viscosity of the component A is less than or equal to 100 mPa·s, and after the component A is mixed with the component B, a viscosity of the double-component gastric ultrasound examination aided developer is more than or equal to 500 mPa·s.

6. A preparation method for the double-component gastric ultrasound examination aided developer according to claim 1, comprising:

- taking pure water, adding citric acid at 50-100 rpm, adjusting a rotation speed to 800-1200 rpm after citric acid is dissolved, adding sodium alginate, then adjusting the rotation speed to 30-60 rpm, heating a solution to 90° C. under continuous stirring, adjusting the rotation speed to 50-100 rpm after sodium alginate is completely dissolved, then adding functionalized silica particles, a defoamer and a preservative to be mixed with the solution to obtain component A;
- dissolving calcium chloride into the pure water at 50-100 rpm to obtain an unsterilized component B;
- respectively charging the component A and the unsterilized component B into a polyester bottle; and
- sterilizing the unsterilized component B under an electronic irradiation of 15-25 K to obtain a component B.

* * * * *